United States Patent [19]
Yoshida

[11] 4,223,790
[45] Sep. 23, 1980

[54] CONTAINER INSPECTION SYSTEM
[75] Inventor: Hajime Yoshida, Tokyo, Japan
[73] Assignee: Hajime Industries, Ltd., Tokyo, Japan
[21] Appl. No.: 877,280
[22] Filed: Feb. 13, 1978
[51] Int. Cl.² .............................................. B07C 5/34
[52] U.S. Cl. ....................................... 209/590; 73/41
[58] Field of Search ..................... 209/590; 73/40, 41, 73/45.1, 45.2, 45.4

[56] References Cited
U.S. PATENT DOCUMENTS

| | | | |
|---|---|---|---|
| 2,635,746 | 4/1953 | Gordon | 209/590 X |
| 3,438,493 | 4/1969 | Goble | 209/590 |
| 3,608,715 | 9/1971 | Snyder et al. | 209/590 |
| 3,802,252 | 4/1974 | Hayward et al. | 209/590 X |

*Primary Examiner*—Joseph J. Rolla
*Attorney, Agent, or Firm*—Thomas R. Morrison

[57] ABSTRACT

A container inspection system is disclosed in which an ultrasonic wave pulse is impinged on an object such as a container to be detected or inspected, the ultrasonic wave pulse modulated with the inherent vibration of the object is received, the modulated ultrasonic wave pulse is converted into a corresponding electrical signal, and the electrical signal is compared with a reference signal for discriminating whether the container is good or not. This system further includes a device for segregating bad and good objects in response to the inspection result thereof.

10 Claims, 10 Drawing Figures

→ Time

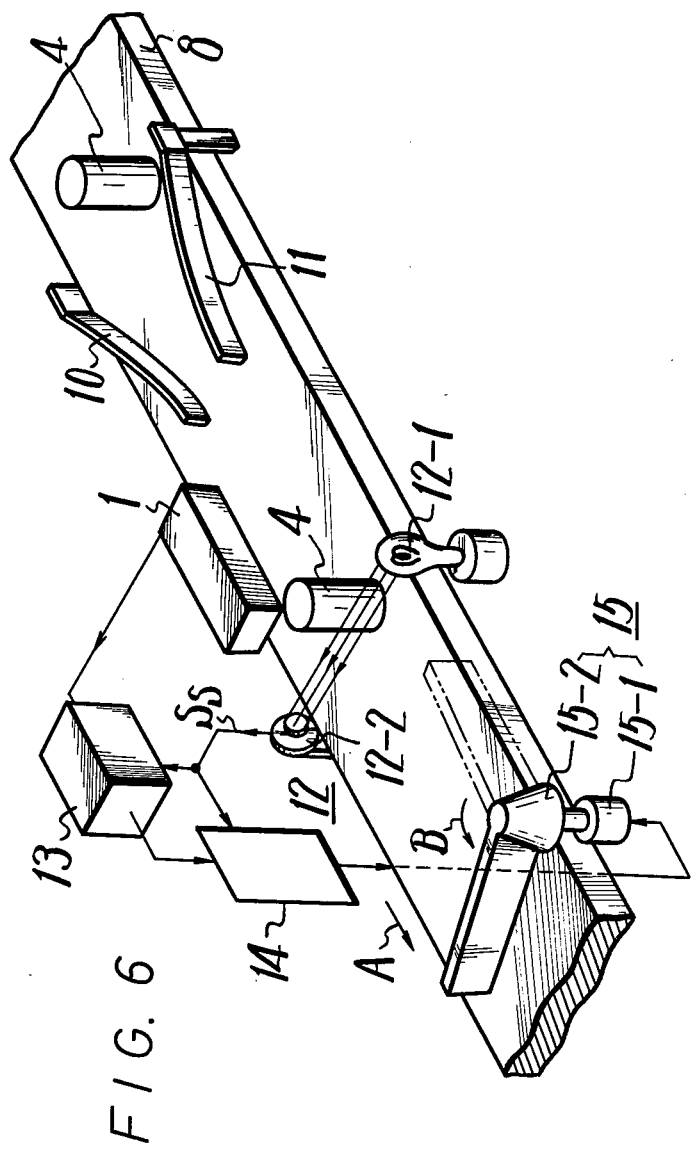
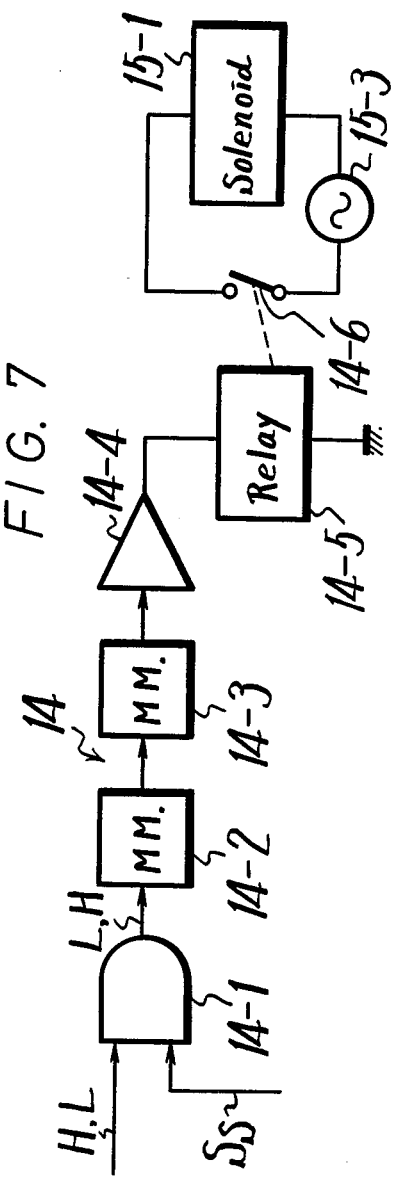

CONTAINER INSPECTION SYSTEM

BACKGROUND OF THE INVENTION

1. Field of the Invention

This invention relates generally to a container inspection system, and is directed more particularly to a container inspection system which enables high speed and reliable discrimination for the good or bad of objects such as containers and the like to be detected or inspected.

2. Description of the Prior Art

Conventionally, the judgement for the internal pressure or inspection of the good or bad of sealed containers such as canned products, was widely dependent on the tapping inspection which relies upon the hearing ability of mankind (sensitivity inspection), whereas during the recent years, methods to inspect the cans by electrical energy or signal transmitted onto the cans to cause vibration of the can and thereby taking measurement of the energy distribution of various frequencies of the electrical signal caused by the vibration of the cans to detect whether the cans are good or not are proposed.

However, by such methods, by the delicate differences such as wall thickness of the can or the rotary sealing degree of the caps of bottles, the energy distribution of the various frequencies are influenced, and further when relatively large electrical energy impacts are given to the containers such as cans, a harmful noise other than the container's inherent resonance frequency is simultaneously generated, which makes it difficult to extract the correct electrical signals related to the internal pressure of the container such as cans and consequently, by the above or conventional methods, there is a drawback where it is impossible to conduct an accurate inspection.

Normally, to erase a noise or to extract the peculiar energy of various frequencies, a complicated electrical processing which requires long processing time is required. Accordingly, by such above mentioned known technology the discrimination of the good or bad of the produced cans that flow on a high speed conveyer remains improper for adoption.

OBJECTS AND SUMMARY OF THE INVENTION

Accordingly, a main object of this invention is to present a container inspection system that can conduct the inspection for good or bad of containers such as can products at high speed and with high reliability.

Another object of the invention is to provide a container inspection system which is simple in construction but highly reliable in inspection.

A further object of the invention is to provide a container inspection system which can segregate bad and good containers in response to the inspection thereof.

According to an aspect of the present invention there is provided a container inspection system which comprises ultrasonic wave transmitting circuit for generating an ultrasonic wave and impinging said ultrasonic wave on an object to be inspected, a circuit for receiving an ultrasonic wave modulated by said object at its inherent vibration; and a circuit for comparing said ultrasonic wave with a reference signal to discriminate good or bad of said object.

The other objects, features and advantages of the invention will become apparent from the following description taken in conjunction with the accompanying drawings in which the like reference numerals designate the like elements.

BRIEF DESCRIPTION OF THE DRAWINGS

FIG. 6 is a schematic perspective diagram showing another example of the invention; and FIG. 7 is a logic diagram showing the driver circuit used in FIG. 6.

DESCRIPTION OF THE PREFERRED EMBODIMENTS

An example of the container inspection system of this invention will be explained hereunder with reference to the drawings.

Figure 1:
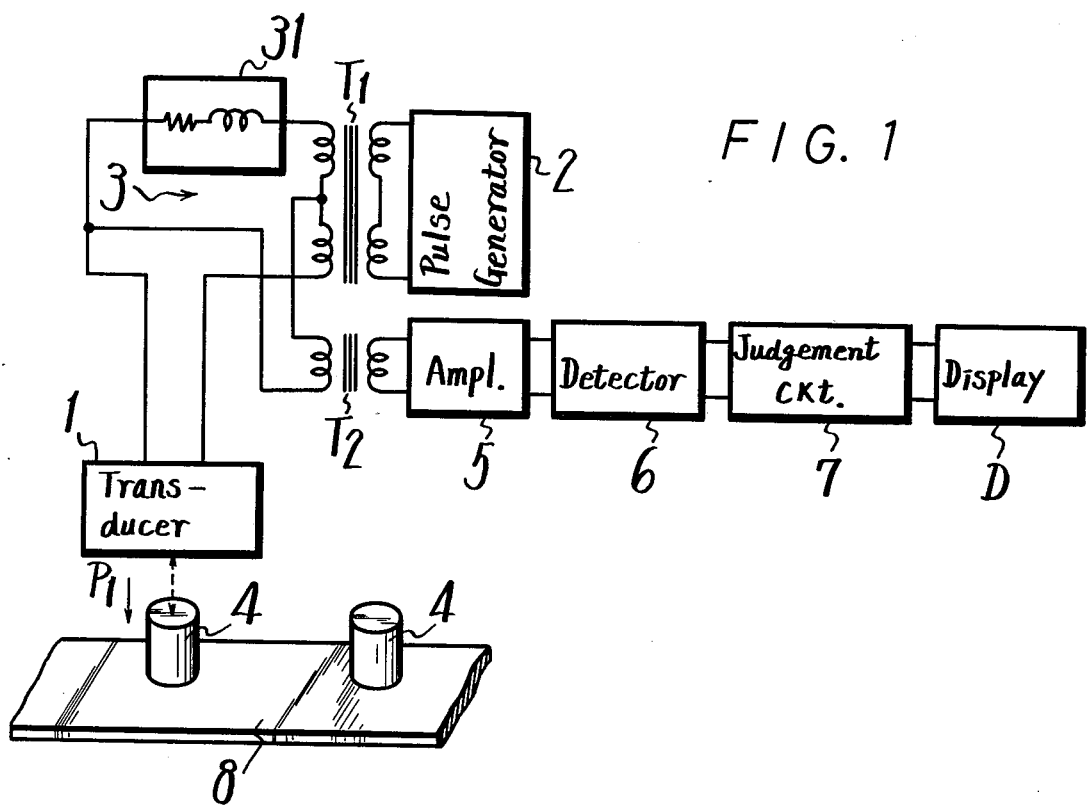
FIG. 1 is a systematic diagram showing an example of the container inspection system according to the present invention.

FIG. 1 is a schematic diagram showing an example of the container inspection system according to this invention. In FIG. 1, 1 designates a transducer or ultrasonic transmitter and receiver unit which is made of, for example, titanium oxide barium ceramics or crystal, or ferrite etc. and reference 2 indicates a pulse generator which produces, for example, an electrical pulse signal with the frequency of about 50–200 $MH_z$ and supplies the same to the transducer 1 through, for example, a transformer T1 and a bridge circuit 3. Then, the transducer 1 transmits a beamlike ultrasonic wave pulse P1 such as shown on FIG. 2A, which has a very short constant time period such as 1–3 milliseconds, for instance. This ultrasonic wave pulse P1 is transmitted onto a container 4 such as can, bottle or the like to be detected or inspected, that is loaded and sealed. At such incidence, the outer wall of container 4 is energized by the ultrasonic wave pulse P1 and delicately vibrates at its inherent frequency in correlation with the inner pressure of container 4, and accordingly, container 4 modifies or modulates the ultrasonic wave pulse P1 from transducer 1 by its inherent vibration. In other words, ultrasonic wave P2 or P3 as shown on FIGS. 2B and 2C are emitted from container 4.

Generally, when the sealed container 4 such as a loaded can or bottle maintains high vacuum (equivalent to a good product), the resonance frequency of container 4 is high, with a high Q, whereas when the vacuum in container 4 is low (equivalent to a bad product), the resonance frequency of container 4 is low, with a low Q. In other words, the ultrasonic wave that is modulated by container 4 which has good vacuum and high Q, is shown on FIG. 2B at P2. This ultrasonic wave P2 is high in vibration energy and continues for a few milliseconds (5 to 6 mill second) as an example. On the other hand, the ultrasonic wave that is modulated by container 4 which has a bad vacuum and low Q, is shown on FIG. 2C at P3. This ultrasonic wave P3 has a low vibration energy than that P2 shown on FIG. 2B and has a shorter continuation period as for instance, 2-3 milliseconds. Accordingly, by taking measurement of the ultrasonic wave energy amount as modulated by container 4, judgement of the good or bad of container 4 can be made. Accordingly, in the example of this invention illustrated on FIG. 1, the ultrasonic wave as modulated by container 4 is received by transducer 1 which converts the received ultrasonic wave into a corresponding electrical signal. This electrical signal is supplied through bridge circuit 3, a transformer T2 and an amplifier 5 to a detection circuit or detector 6 to detect the energy of the modulated ultrasonic wave or corresponding electrical signal. As the next step, the output of detection circuit 6 is supplied to a good and bad judgement circuit 7 in which the output of detector 6 is compared with a predetermined reference value which represents the energy value of a good product of the container in order to discriminate the good or bad thereof. The output of judgement circuit 7 is applied to a display or alarm device D to display good or bad of the container.

Figure 3:
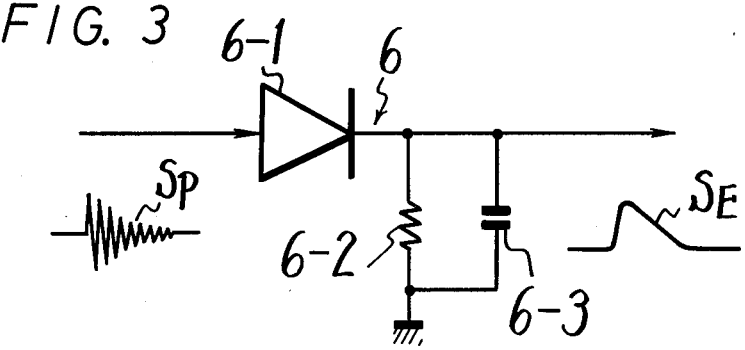
FIG. 3 is a schematic diagram showing an example of the detector used in FIG. 1.

Now, a practical example of the detector 6 used in the example of the present invention shown in FIG. 1 is illustrated in FIG. 3. As shown in FIG. 3, the detector 6 consists of a diode 6-1, a resistor 6-2 connected between the output side of diode 6-1 and the ground, and a capacitor 6-3 connected in parallel to the resistor 6-2. As set forth above, the output signal $S_p$ of amplifier 5 is fed to the detector 6 which then produces an envelope signal $S_E$ from the signal $S_P$. This envelope signal $S_E$ is applied to the judgement circuit 7.

Figure 4:
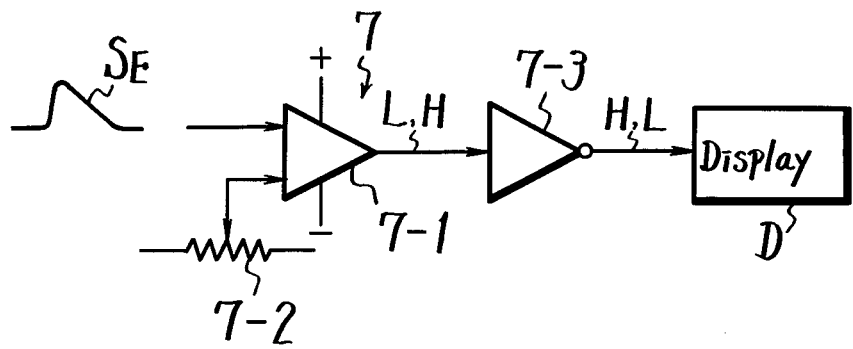
FIG. 4 is a schematic diagram showing an example of the judgement circuit used in FIG. 1.
Figure 5A:
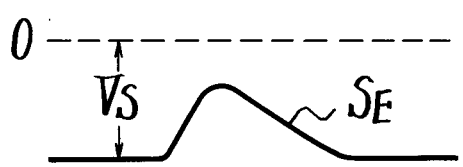
FIGS. 5A and 5B are waveform diagrams used for explaining the invention.
Figure 5B:
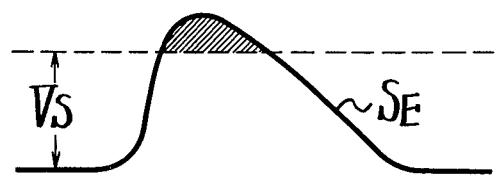

FIG. 4 is a circuit diagram showing a practical example of judgement circuit 7. As shown in FIG. 4, the judgement circuit 7 includes a level comparator 7-1, which is supplied with the output signal $S_E$ from detector 6 at its one input terminal, and a reference voltage set device 7-2 such as a potentiometer whose movable tap is connected to the other input terminal of the level comparator 7-1, the potentiometer 7-2 serving to set a desired threshold or reference voltage $V_S$ shown on FIGS. 5A and 5B. This level comparator 7-1 produces an output signal, for example, when the input signal $S_E$ has such a level that exceeds the threshold voltage $V_S$ as shown on FIG. 5B. In practice, however, since a bad container, which corresponds to the signal $S_E$ of low level as shown in FIG. 5A, is desired to be removed or segregated (which will be described later), the level comparator 7-1 is so formed that it generally delivers a low output signal L (or zero voltage) and the output signal of level comparator 7-1 is the low output signal L when the level of signal $S_E$ does not exceed the threshold voltage $V_S$ (corresponding to a bad container) a shown on FIG. 5A. While, when the signal $S_E$, whose level exceeds the threshold voltage $V_S$ (corresponding to a good container) as shown in FIG. 5B, is applied to the level comparator 7-1, it produces a high output signal H. The output signal L or H from level comparator 7-1 is applied to an inverter 7-3 to be inverted as a high or low signal H or L. The output signal H or L from the inverter 7-3 is applied to the display device D, so that the display device D displays that the inspected container is bad or good in response to the output signal H or L from judgement circuit 7 or inverter 7-3, for example, when the signal H is applied to the display device D, it lights a lamp (not shown) to display that the inspected container is bad.

Figure 2A:
FIGS. 2A, 2B and 2C are waveform diagrams used for explaining the operation of the invention shown in FIG. 1.
Figure 2B:
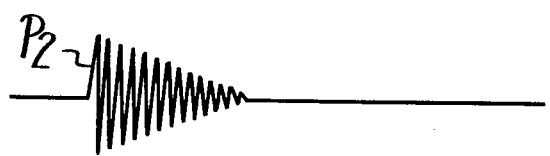
Figure 2C:
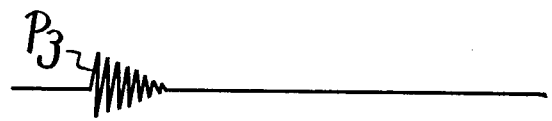

In this invention, the specifically timed electrical signal or pluse P1 as shown on FIG. 2A is supplied to transducer 1 through transformer T1 and bridge circuit 3 from the pulse generator 2, but the pulse signal from the pulse generator 2 is not supplied to amplifier 5, whereas, of course, the transducer 1 receives the modulated ultrasonic wave P2 or P3 from container 4 and supplies only the corresponding electrical signal to amplifier 5 through bridge circuit 3 and transformer T2. Note that on FIG. 1, 31 designates balancing circuit for the bridge circuit 3. As an alternative, such circuit construction may be used in which bridge circuit 3 is not used and while the transducer 1 is transmitting the ultrasonic wave, amplifier 5 stops its function with the same effect as above mentioned. Further, in place of one transducer 1, two transducers may be separately installed for ultrasonic wave transmittance and receiving, to obtain the same results.

In the case of consecutively inspecting containers 4, which are continuously transferred by a belt conveyer 8, the system of this invention has a short time selected such as 1-3 milliseconds for the ultrasonic waves generation, and the generation period of the modulated ultrasonic waves by the containers 4 to be inspected is also a very short time such as within a few milliseconds, so that the present invention makes it simple to consecutively and automatically inspect the containers 4 which are transferred on belt conveyer 8 or to conduct high speed inspection.

As explained above, according to the system of this invention, an ultrasonic wave pulse is transmitted on an object to be inspected for a very short time period, the ultrasonic wave pulse, modulated by the inspection object is received, this modulated ultrasonic wave is converted in to a corresponding electrical signal, the energy value of this electrical signal is compared with the energy value of the reference signal representing a good product, and the good or bad of the object to be inspected is judged, so that the discrimination result of good or bad of the container is accurate and highly reliable, and in addition, it is possible to accurately and reliably inspect objects which are consecutively conveyed at a high speed.

The above mentioned container inspection system of this invention can be used, for example, to segregate good and bad containers, as illustrated on FIG. 6, in which elements same as those in FIG. 1 are marked with the same numerals. FIG. 6 shows another example of this invention in which the container inspection system of this invention set forth above is placed after the container completion equipment at a proper location, for instance, in the lineway to the storage place of such containers 4, which are conveyed by conveyer belt 8 to be discriminated good or bad. For such purpose, as shown on FIG. 6, guides such as 10 and 11 are installed in relation to the conveyer belt 8, so that the containers 4 that are conveyed by conveyer belt 8 pass through a predetermined location.

Related to this predetermined location, there is provided a location finder system 12 to indicate that the containers 4 have arrived at such location, which comprises a light source such as a lamp 12-1 and a photo electric conversion element 12-2 such as a photocell, which are placed, for example, near the both sides of the conveyer belt 8, so that when the containers 4 arrive between the two, the location finder system 12 indicates such an arrival by generating an electrical signal.

On FIG. 6, the transducer 1, which impinges ultrasonic wave pulse onto the container 4 in relation to the moving direction A of the conveyer belt 8 as set forth previously in connection with FIG. 1, is positioned at the upper front of the location finder system 12. Now, when container 4 is conveyed on conveyer belt 8 and arrives at the above predetermined location, such arrival is detected by location finder system 12 or photocell 12-2 which generates an electrical signal $S_S$ at this time. This electrical signal $S_S$ is fed to mainbody 13, which contains the pulse generator 2 and electric circuitry, mainly consisting of the discrimination or judgement circuit 7 as described in connection with FIG. 1, to start this system.

At such instance, the mainbody 13 is started, whereas transducer 1 transmits an impinging ultrasonic signal, and consecutively functions as previously described to judge the good or bad of the container. For instance, when the container 4 is bad, an electrical signal such as high signal H is generated from good or bad discrimination or judgement circuit 7 or inverter 7-3, which is contained in the circuitry of the main body 13. This high signal H is fed through a drive circuit 14, which is described later, to a rotary solenoid 15-1 of a container segregation system 15 which is installed after the location finder system 12 related to the moving direction A of conveyer belt 8. This segregation system 15 contains an arm 15-2 which is rotated by rotary solenoid 15-1 when it is driven. Generally, the arm 15-2 of segregation system 15 is not placed in contact with the upper surface of the conveyer belt 8 but above it with a small gap, so that the arm 15-2 does not bother the movement of the containers 4 as being conveyed, (refer to 2-dot chain line position on FIG. 6), but when the container 4 is judged as bad, the discrimination circuit 7 or inverter 7-3 generates an electric signal H, which is fed to the rotary solenoid 15-1 of the segregation system 15, by which arm 15-2 is rotated above the top of the conveyer belt 8 in a direction B, so that the bad container 4 is segregated by the arm 15-2 to a certain location off conveyer belt 8.

Now, the above drive circuit 14 will be described with reference to FIG. 7. In the drive circuit 14 there is provided an AND gate circuit 14-1 which is supplied at its one input terminal with the output signal H or L from inverter 7-1 of the judgement circuit 7 (FIG. 4) and at its other input terminal with the electrical signal $S_S$ (which corresponds to a high signal H and represents the arrival of a container at a predetermined location) from the location finder system 12 or photocell 12-2. When no container 4 arrives at the predetermined location, the location finder system 12 produces a low output signal L or no electric signal $S_S$. When the system 12 produces no signal, the AND gate 14-1 is so formed that it produces a low output signal L or does not produce any signal regardless of the output signals H and L from the inverter 7-3, but it produces a high output signal H only when the finder system 12 produces signal $S_S$ (high signal H) upon arrival of container 4 and the inverter 7-3 delivers high signal H upon detecting bad container 4. Even if the signal $S_S$ (high signal H) is fed to AND gate 14-1 which is also supplied with the low signal L (corresponding to a good container) from the inverter 7-3, the AND gate 14-1 does not produce a high signal H but produces a low signal L or no signal. The output L or H from AND-gate 14-1 is fed to mono-multivibrators 14-2 and 14-3 to be delayed by a predetermined period because the segregating system 15 is located downstream the inspection system and finder system 12. When the AND gate 14-1 produces high signal H (which means that a container arrived at the predetermined location is inspected as bad), this signal is fed through the mono-multivibrators 14-2 and 14-3 and a driver 14-4 to a relay coil 14-5 to energize the latter. Thus, its normally opened relay contact 14-6, which is connected in series to a series circuit of the solenoid 15-1 and its power source 15-3, is closed by the energization of relay coil 14-5 and hence the solenoid 15-1 is energized to rotate the arm 15-2 from the 2-dot chain line position to its solid line position (in FIG. 6) to remove the bad container off the belt 8. Thereafter, the relay 14-5 is de-energized immediately, hence the contact 14-6 is opened as normal and the solenoid 15-1 is de-energized to return the arm 15-2 to its original position (2-dot chain line position in FIG. 6).

If a container arrived at the predetermined location is good, the relay 14-5 is not energized and hence the solenoid 15-1 is not energized also. Thus, the arm 15-2 remains at its 2-dot chain line position and the inspected container is transported by the belt 8 to the direction A as it is.

In this latter example, it is possible to assemble the display device D to the main body 13 so as to display the arrival of a bad container.

The above explanations are applied to the preferred examples of the invention to discriminate the good or bad of sealed containers such as loaded cans to segregate the same. However, it will be apparent that this invention is not necessarily limited to the discrimination of good or bad for sealed containers such as loaded cans, etc., but can naturally be applied to the inspection of containers and material, etc., which display the same effect as explained above against ultrasonic waves and many variations or modifications may be effected by one skilled in the art without departing from the spirits or scope of the novel concepts of this invention. Therefore, the scope of the invention should be determined by the appended claims.

I claim as my invention:

1. An object inspection system comprising:
   (a) ultrasonic wave transmitting means positioned a substantial distance apart from an object to be inspected for generating an ultrasonic wave for a constant time period and impinging said ultrasonic wave on said object;
   (b) means for receiving a modulated ultrasonic wave after the end of said time period modulated by said object at its inherent vibration frequency in response to the energy of said applied ultrasonic wave;
   (c) means for producing an electrical signal corresponding to said modulated ultrasonic wave; and
   (d) means for comparing said electrical signal with a reference signal to discriminate at least one property of said object.

2. An object inspection system as claimed in claim 1, in which said ultrasonic wave transmitting means includes a pulse generator, a transformer, a bridge circuit and a transducer.

3. An object inspection system as claimed in claim 1, in which said modulated ultrasonic wave receiving means includes transducer means for converting said modulated ultrasonic wave into a corresponding electrical signal.

4. An object inspection system as claimed in claim 3, in which said comparing means includes a detector receiving said corresponding electrical signal, and a judgement circuit receiving an output signal of said detector and comparing the same with the reference signal corresponding to said at least one property.

5. An object inspection system comprising:
(a) ultrasonic wave transmitting means positioned a substantial distance apart from an object to be inspected for generating an ultrasonic wave for a constant time period and impinging said ultrasonic wave on said object;
(b) conveyor means for conveying said object near said ultrasonic wave transmitting means;
(c) means for receiving an ultrasonic wave after the end of said time period modulated by said object at its inherent vibration frequency in response to the energy of said applied ultrasonic wave;
(d) means for producing an electrical signal corresponding to said modulated ultrasonic wave;
(e) means for comparing said electrical signal with a reference signal to discriminate at least one property of said object;
(f) means for detecting an arrival of said object at a predetermined position and for driving said ultrasonic wave transmitting means and impinging said ultrasonic wave on said predetermined position; and
(g) means for segregating said object in response to the discrimination of said comparing means.

6. A container inspection system according to claim 5 further comprising means for guiding said object to said predetermined position.

7. A method for inspecting an object comprising:
(a) generating an ultrasonic pulse for a predetermined time;
(b) impinging said ultrasonic pulse on said object from a position spaced a substantial distance apart from said object;
(c) modulating said ultrasonic pulse by said object at its inherent vibration frequency in response to the energy of the applied ultrasonic wave to produce a modulated ultrasonic signal;
(d) detecting said modulated ultrasonic signal after the end of said predetermined time; and
(e) judging at least one property of said object on the basis of the detected modulated ultrasonic signal.

8. The method recited in claim 7 further comprising:
(a) said ultrasonic pulse having a frequency of from about 50 to about 200 megahertz; and
(b) said ultrasonic pulse is generated for a time period of less than 3 milliseconds.

9. The method recited in claim 7 further comprising:
(a) moving a plurality of said objects past said ultrasonic pulse source;
(b) detecting when each of said plurality is positioned for inspection; and
(c) diverting at least some of said objects on the basis of said judging.

10. The method recited in claim 7 wherein said judging step is performed by comparing the result of said detecting step with a reference signal.

* * * * *